(12) United States Patent
Avirovikj et al.

(10) Patent No.: US 12,097,046 B2
(45) Date of Patent: Sep. 24, 2024

(54) WEARABLE CONTINUOUS ANALYTE MEASUREMENT DEVICES, BIOSENSOR INSERTERS, AND METHODS OF USE

(71) Applicant: Ascensia Diabetes Care Holdings AG, Basel (CH)

(72) Inventors: Dragan Avirovikj, Stamford, CT (US); Jon Taylor, Groton, MA (US)

(73) Assignee: Ascensia Diabetes Care Holdings AG, Basel (CH)

( * ) Notice: Subject to any disclaimer, the term of this patent is extended or adjusted under 35 U.S.C. 154(b) by 33 days.

(21) Appl. No.: 17/581,844

(22) Filed: Jan. 21, 2022

(65) Prior Publication Data

US 2022/0225939 A1    Jul. 21, 2022

Related U.S. Application Data

(60) Provisional application No. 63/140,180, filed on Jan. 21, 2021.

(51) Int. Cl.
*A61B 5/00* (2006.01)
*A61B 5/1486* (2006.01)

(52) U.S. Cl.
CPC ........ *A61B 5/6849* (2013.01); *A61B 5/14865* (2013.01); *A61B 5/6832* (2013.01); *A61B 2560/063* (2013.01)

(58) Field of Classification Search
CPC ............ A61B 5/14532; A61B 5/14546; A61B 5/1455; A61B 5/1459; A61B 5/1477; A61B 5/1486–14865; A61B 5/6801; A61B 5/6833–68335; A61B 5/688; A61B 2560/0406–0412; A61B 2560/0443–045; A61B 2562/16; A61B 2562/164–166; A61B 5/14503; A61B 5/1473–14735;
(Continued)

(56) References Cited

U.S. PATENT DOCUMENTS 8,333,714 B2    12/2012  Stafford
8,862,198 B2    10/2014  Stafford
(Continued)

FOREIGN PATENT DOCUMENTS

CN    101268932 A    9/2008
CN    100591265 C    2/2010
(Continued)

OTHER PUBLICATIONS

Machine Translation: EP 2422693 (Year: 2024).*
(Continued)

*Primary Examiner* — Navin Natnithithadha
*Assistant Examiner* — Alice Ling Zou
(74) *Attorney, Agent, or Firm* — Erise IP, P.A.

(57) ABSTRACT

A continuous analyte monitor wearable device. The wearable device includes a primary portion comprising at least a sensor assembly comprising a biosensor, and a secondary portion comprising a pocket configured to receive a transmitter unit and a sealable opening to the pocket, the sealable opening containing an adhesive on edges thereof; and a backing member provided over the adhesive wherein removing the backing member exposes the adhesive to seal the sealable opening and encapsulate the transmitter unit. Biosensor inserters and method of using the biosensor inserter are also provided.

13 Claims, 15 Drawing Sheets

(58) Field of Classification Search
CPC .......... A61B 17/3468; A61B 2560/063; A61B 5/1451–14514; A61B 5/6832–68335; A61B 5/6848–6894
See application file for complete search history.

(56) References Cited

U.S. PATENT DOCUMENTS

| | | | |
|---|---|---|---|
| 9,662,071 | B2 | 5/2017 | Ohkoshi |
| 9,980,670 | B2 | 5/2018 | Funderburk et al. |
| 10,292,632 | B2 | 5/2019 | Lee et al. |
| 11,160,926 | B1* | 11/2021 | Halac .................. A61M 15/008 |
| 2008/0027296 | A1 | 1/2008 | Hadvary et al. |
| 2008/0097246 | A1 | 4/2008 | Stafford et al. |
| 2008/0319414 | A1 | 12/2008 | Yodfat et al. |
| 2009/0257911 | A1 | 10/2009 | Thomas et al. |
| 2010/0198033 | A1 | 8/2010 | Krulevitch et al. |
| 2011/0060196 | A1* | 3/2011 | Stafford ................ A61B 5/0002 343/909 |
| 2011/0077490 | A1* | 3/2011 | Simpson ............... A61B 5/1468 600/345 |
| 2011/0106126 | A1 | 5/2011 | Love et al. |
| 2011/0279963 | A1* | 11/2011 | Kumar .................. A61B 5/291 156/60 |
| 2012/0157801 | A1 | 6/2012 | Hoss et al. |
| 2012/0197098 | A1 | 8/2012 | Donnay et al. |
| 2013/0150691 | A1 | 6/2013 | Pace et al. |
| 2013/0267811 | A1 | 10/2013 | Pryor et al. |
| 2014/0066730 | A1 | 3/2014 | Roesicke et al. |
| 2015/0018639 | A1 | 1/2015 | Stafford |
| 2016/0058344 | A1 | 3/2016 | Peterson et al. |
| 2016/0058474 | A1 | 3/2016 | Peterson et al. |
| 2016/0213322 | A1* | 7/2016 | Goldberg ............... A61M 25/02 |
| 2017/0143243 | A1 | 5/2017 | Deck |
| 2017/0202488 | A1 | 7/2017 | Stafford |
| 2017/0245798 | A1 | 8/2017 | Ohkoshi |
| 2018/0116570 | A1 | 5/2018 | Simpson et al. |
| 2018/0116572 | A1 | 5/2018 | Simpson et al. |
| 2018/0325433 | A1 | 11/2018 | Prais et al. |
| 2018/0368774 | A1 | 12/2018 | Gray et al. |
| 2019/0021636 | A1* | 1/2019 | Walter .................. A61B 5/6849 |
| 2019/0223768 | A1 | 7/2019 | Muller et al. |
| 2020/0009745 | A1 | 1/2020 | Grossard et al. |
| 2020/0100713 | A1 | 4/2020 | Simpson et al. |
| 2020/0214633 | A1 | 7/2020 | Antonio et al. |
| 2020/0337642 | A1* | 10/2020 | Garai .................. A61B 5/14532 |
| 2021/0052301 | A1 | 2/2021 | Gass et al. |
| 2021/0052302 | A1 | 2/2021 | Erekovcanski et al. |
| 2021/0228156 | A1* | 7/2021 | Kouge ................. H05K 5/0086 |
| 2022/0071528 | A1 | 3/2022 | Avirovikj et al. |

FOREIGN PATENT DOCUMENTS

| | | | | |
|---|---|---|---|---|
| CN | 102065908 | A | 5/2011 | |
| CN | 103826528 | A | 5/2014 | |
| EP | 2422693 | A1 * | 2/2012 | ......... A61B 5/14532 |
| EP | 2636372 | A1 | 9/2013 | |
| EP | 2826422 | A1 | 2/2015 | |
| EP | 3170453 | A1 | 5/2017 | |
| EP | 3449827 | A1 | 3/2019 | |
| JP | 2008508971 | A | 3/2008 | |
| JP | 2008246204 | A | 10/2008 | |
| JP | 2015509011 | A | 3/2015 | |
| WO | WO-2011119898 | A1 * | 9/2011 | ............. A61B 17/34 |
| WO | WO2013090215 | A2 | 6/2013 | |
| WO | WO2016036924 | A2 | 3/2016 | |
| WO | WO2018027940 | A1 | 2/2018 | |
| WO | WO2018195286 | A1 | 10/2018 | |
| WO | WO2018206552 | A1 | 11/2018 | |
| WO | WO2019054113 | A1 | 3/2019 | |
| WO | WO2019176324 | A1 | 9/2019 | |

OTHER PUBLICATIONS

U.S. Appl. No. 17/581,842, filed Jan. 21, 2022, Avirovikj et al.
International Search Report and Written Opinion of International Application No. PCT/EP2022/051312 mailed May 11, 2022.
PCT Patent Application PCT/EP2022/051312 International Preliminary Report on Patentability issued Jan. 24, 2023.
European Patent Application 22702648.1 Office Action issued Jul. 31, 2024.

* cited by examiner

WEARABLE CONTINUOUS ANALYTE MEASUREMENT DEVICES, BIOSENSOR INSERTERS, AND METHODS OF USE

CROSS REFERENCE TO RELATED APPLICATION

This claims the benefit of U.S. Provisional Patent Application No. 63/140,180, filed Jan. 21, 2021, the disclosure of which is hereby incorporated by reference herein in its entirety for all purposes.

FIELD

The present disclosure relates to wearable continuous analyte measurement (CAM) devices and to biosensor inserters configured to insert a biosensor of the wearable CAM device.

BACKGROUND

Continuous glucose monitoring, such as with a continuous glucose monitor (CGM), has become a routine sensing operation, particularly for sensing blood glucose in relationship to diabetes care. By providing real-time glucose monitoring that provides glucose concentration readings over time, therapeutic actions, such as insulin uptake or other actions, may be undertaken in a timely manner and the glycemic condition may be better controlled.

During CGM operation, a biosensor of a transmitter and sensor assembly is inserted subcutaneously and is continuously operated in an environment surrounded by tissue and interstitial fluid (ISF). The biosensor inserted under the skin provides a signal to a transmitter of the transmitter and sensor assembly, and that signal can be indicative of a patient's blood glucose level, for example. These measurements may be made intermittently and automatically many times throughout the day (e.g., every few minutes or at any other suitable interval).

The transmitter and sensor assembly is adhered to the outer surface of a user's skin, such as on the abdomen or on the back of the upper arm, while the biosensor is inserted through the skin so as to contact ISF. This skin insertion process may be referred to as "insertion." Devices for carrying out this biosensor insertion may be referred to as "biosensor inserters."

SUMMARY

In some embodiments, a CAM wearable device configured to measure an analyte concentration is provided. The CAM wearable device includes a primary portion comprising at least a sensor assembly comprising a biosensor, a secondary portion comprising a pocket configured to receive a transmitter unit and a sealable opening to the pocket, the sealable opening containing an adhesive on edges thereof, and a backing member provided over the adhesive wherein removing the backing member exposes the adhesive to seal the sealable opening and encapsulate the transmitter unit.

In some embodiments, a biosensor inserter configured to insert a biosensor of a wearable device is provided. The biosensor inserter includes a push member, a contact member translatable relative to the push member, and a relief formed in the push member or contact member, the relief configured to allow a secondary portion of the wearable device to be folded into the relief.

In further embodiments, a method of using a biosensor inserter to insert a biosensor of a wearable device is provided. The method includes providing a biosensor inserter comprising: a push member, a contact member translatable relative to the push member, a trocar assembly including a trocar, and a relief formed in the push member or contact member, the relief configured to allow a secondary portion of the wearable device to be folded into the relief, and a mechanism configured to translate the wearable device and insert the trocar, folding the secondary portion of the wearable device into the relief, contacting the contact member to a person's skin, pushing on the push member during a first portion of a stroke to cause translation and implantation of the trocar and biosensor, and continuing to push the push member causing the mechanism to retract the trocar assembly while leaving the biosensor implanted during a second portion of the stroke.

Other features, aspects, and advantages of embodiments in accordance with the present disclosure will become more fully apparent from the following detailed description, the claims, and the accompanying drawings by illustrating a number of example embodiments. Various embodiments in accordance with the present disclosure may also be capable of other and different applications, and its several details may be modified in various respects, all without departing from the scope of the claims and their equivalents. Thus, the description is to be regarded as illustrative in nature, and not as restrictive.

BRIEF DESCRIPTION OF THE DRAWINGS

The drawings are to be regarded as illustrative in nature, and not as restrictive. The drawings are not necessarily drawn to scale. Like numerals are used throughout the drawings to denote like elements.

DETAILED DESCRIPTION

A biosensor inserter is configured to implant (insert) a biosensor of a transmitter and sensor assembly into the skin of a person. In conventional biosensor inserters, a trocar is used as part of the biosensor inserter wherein the trocar aids in the insertion of the biosensor into the skin of the person. Once the biosensor insertion process is performed, the trocar is retracted by operation of the biosensor inserter and generally remains inside of the biosensor inserter. Because blood may contaminate the trocar and biosensor inserter, conventional biosensor inserters are typically treated as a biohazard and are disposed of as medical waste, much like sharps.

Prior biosensor inserter designs may be large and costly to manufacture and generate a large amount of waste, typically discarded as medical waste. Moreover, sensor and transmitter assemblies tend to be rigid and relatively costly to manufacture. In order to reduce the amount of medical waste generated through use of these biosensor inserters, embodiments of the present disclosure operate to minimize the size of the biosensor inserter. In one or more embodiments described herein, the size is reduced by reducing the footprint of the biosensor inserter. This is accomplished by facilitating a foldable wearable device that is configured to fold into a recess or relief of the biosensor inserter. Thus, the overall footprint of the biosensor inserter can be reduced substantially, such as by 50% or more. As such, a volume of the components of the biosensor inserter that are treatable as medical waste are also substantially reduced. Thus, the amount of medical waste to be disposed of is dramatically reduced. Moreover, less material is needed for the biosensor inserter so the cost can be substantially reduced as well.

Figure 1A:
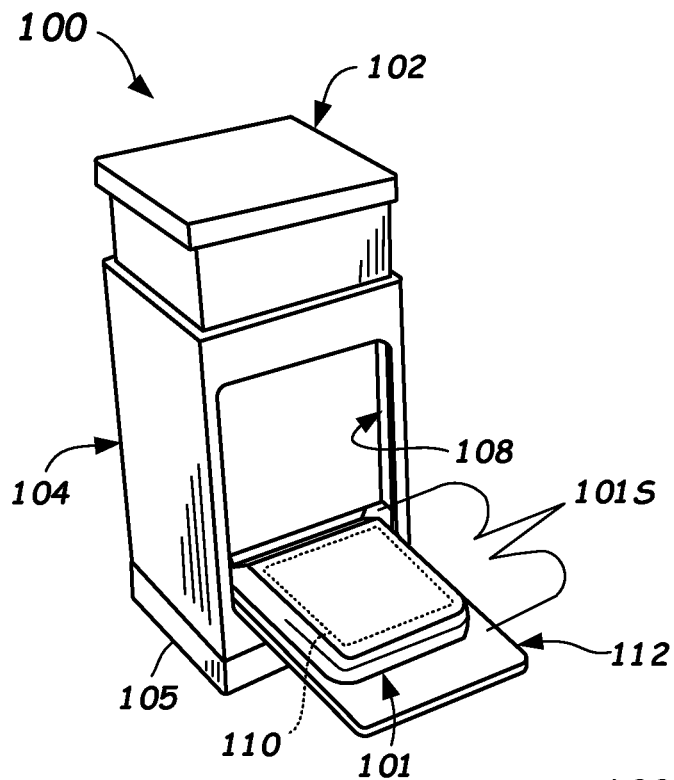
FIG. 1A is a side perspective view of a biosensor inserter including an opened door enabling insertion of a wearable device in accordance with one or more embodiments provided herein.
Figure 1B:
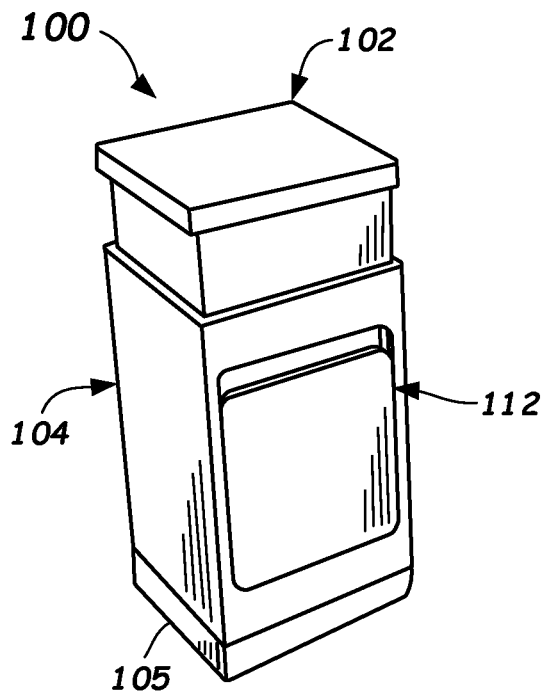
FIG. 1B is a side perspective view of a biosensor inserter including a closed door enabling folding of the wearable device into a recess in the biosensor inserter in accordance with one or more embodiments provided herein.

In accordance with some embodiments of the disclosure, and as shown in FIGS. 1A and 1B, a biosensor inserter 100 is provided that includes a push member 102 configured to be pushed by a user (the person receiving the biosensor or another person), a contact member 104 configured to contact the person's skin, and an internal mechanism (310—FIGS. 3A-3F) that is part of the biosensor inserter 100, and that enables the insertion of a biosensor of a wearable device 101.

Figure 2A:
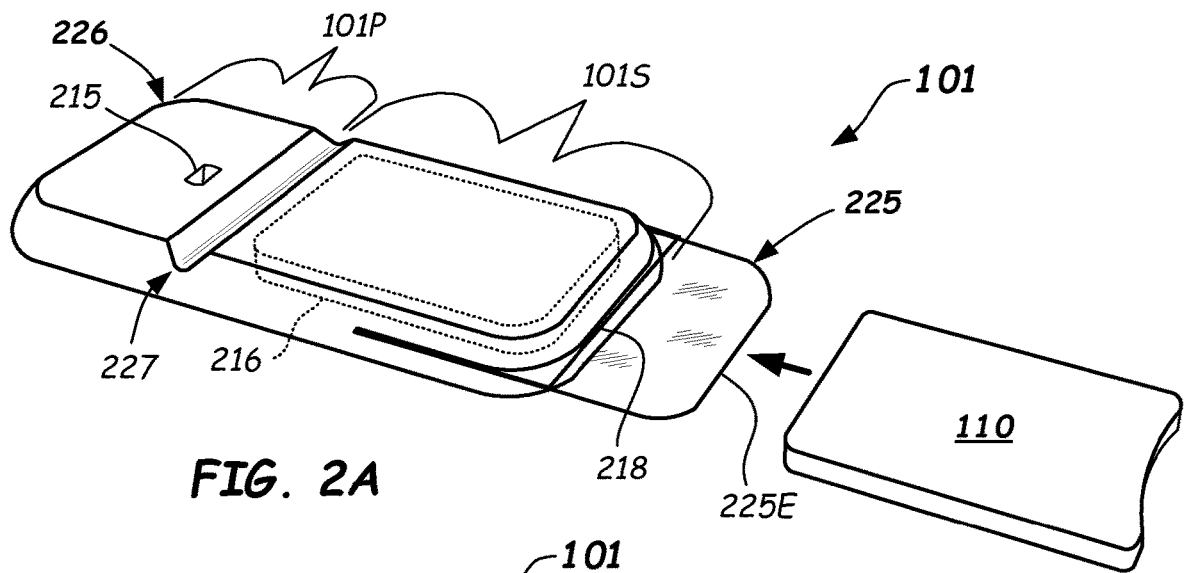
FIG. 2A is a perspective view of a wearable device having a removable and reusable transmitter unit to be inserted and sealed into a pocket in accordance with one or more embodiments provided herein.
Figure 2B:
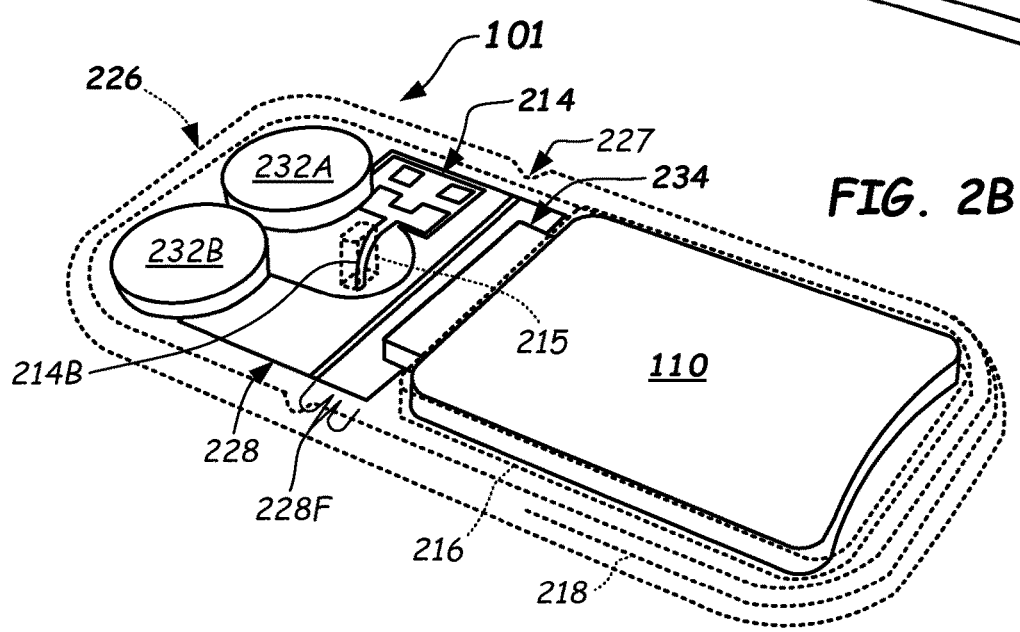
FIG. 2B is a perspective view of a wearable device with a removable transmitter unit being installed in the pocket and illustrating various internal components and a hinge allowing localized bending and thus folding of the wearable device in accordance with one or more embodiments provided herein.
Figure 2C:
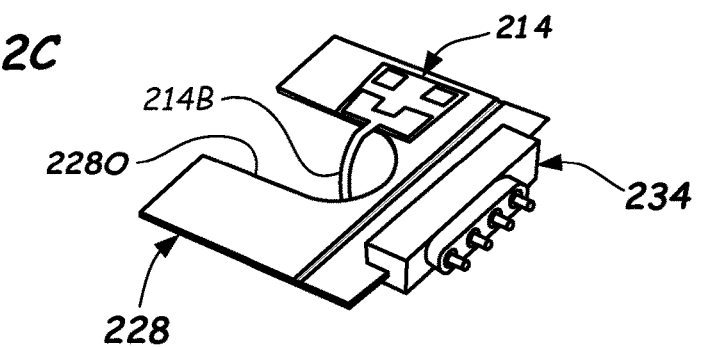
FIG. 2C is a perspective view of a circuit board of a wearable device with a pogo pin type of electrical connector configured to electrically couple with a transmitter unit in the pocket in accordance with one or more embodiments provided herein.
Figure 2D:
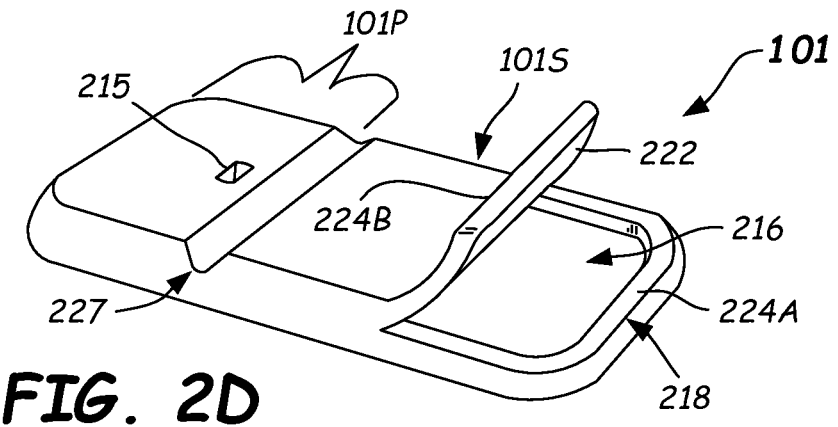
FIG. 2D is a perspective view of a wearable device illustrating the pocket and an opening configured to receive the transmitter unit in accordance with one or more embodiments provided herein.
Figure 2E:
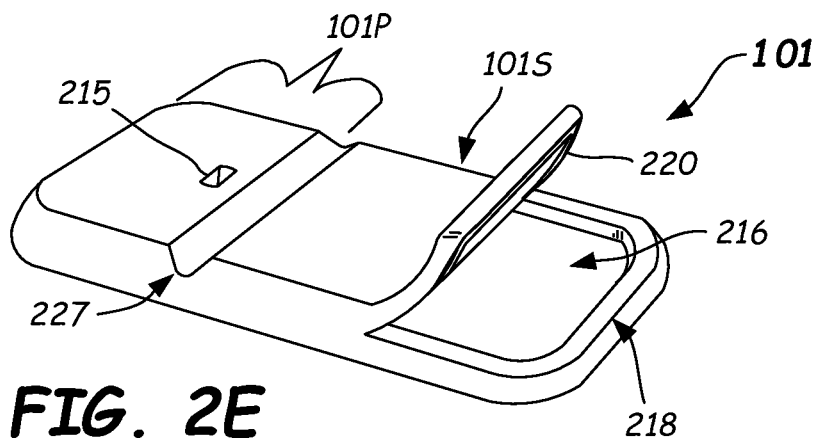
FIG. 2E is a perspective view of a wearable device illustrating the pocket and inclusion of an adhesive on edges of an opening to the pocket in accordance with one or more embodiments provided herein.
Figure 2F:
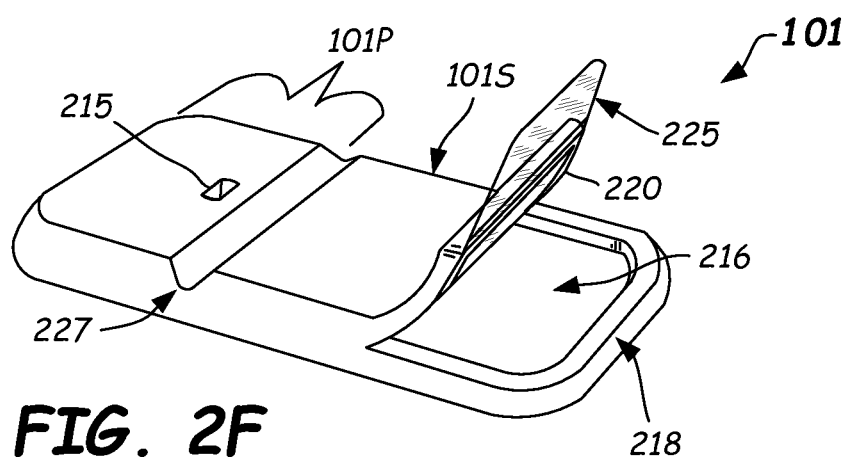
FIG. 2F is a perspective view of a wearable device illustrating an addition of a backing member overtop of the adhesive in the opening in accordance with one or more embodiments provided herein.

In order to better understand the biosensor inserter 100, it is desirable to first understand in more detail an example embodiment of a continuous analyte monitor wearable device 101 (otherwise referred to as "wearable device 101" herein) that is useable with the biosensor inserter 100. Referring now to FIG. 2A through FIG. 2F, an example embodiment of a wearable device 101 is described. Wearable device 101 comprises a primary portion 101P and a secondary portion 101S that is bendable and foldable relative to the primary portion 101P. Primary portion 101P comprises at least a sensor assembly 214, which can be mounted to a circuit board 228. As shown in FIGS. 2B and 2C sensor assembly 214 comprises a biosensor 214B, which is a strand-like sensor element positioned in opening 228O and that can be positioned in and extend within an aperture 215 formed in a body 226 of the wearable device 101. A trocar assembly is receivable in the aperture 215. (A trocar may also be referred to as an insertion portion.)

The secondary portion 101S comprises a pocket 216 configured to receive a transmitter unit 110 and an opening 218 to the pocket 216. The opening 218 is sealable by any suitable means such as by containing an adhesive 220 on at least some of the edges 222 thereof. For example, as shown, the pocket 216 may be formed by an internal space and the opening 218 can comprise a slit opening forming flaps 224A, 224B that are sealable to one another to form a sealed pocket.

Once an adhesive 220 is applied, a backing member 225 (FIG. 2F) can be provided over the adhesive 220. Backing member 225 can be a thin plastic sheet folded partially back over itself, for example. Other configurations of the backing member 225 are possible. After the user inserts the transmitter unit 110 in the pocket 216 through opening 218 and connects the transmitter unit 110 to electrical connector 234 exposed in pocket 216 to make electrical connection therewith, the user can remove the backing member 225 by pulling on an exposed end 225E thereof with thumb and finger. This operates to expose the adhesive 220 and seal the opening 218 and encapsulate the transmitter unit 110. The elastic resilience of the body 226 may provide enough force to cause the flaps 224A, 224B to seal together, but if not the user may apply additional pressure to fully seal the edges of the flaps 224A, 224B to one another.

As should be understood, the transmitter unit 110 contains transmitter components configured and operational to wirelessly transmit data, such as measured analyte data, to a receiving unit, such as a reader or a smart phone executing a software application for storing and/or displaying analyte concentrations. Transmitter unit 110 can also include other electronic components, such as an analog front end for biasing the analyte sensor and for sensing current that passes through the biosensor, such as operational amplifiers, current sensing circuitry, etc. Other transmitter circuitry may include processing circuitry such as analog-to-digital converters for digitizing current signals, memory for storing digitized current signals, and a controller such as a microprocessor, microcontroller, or the like for possibly computing analyte concentration values based on measured current signals.

Now describing the biosensor inserter 100 and its operation in more detail, reference is made to FIGS. 1A-1B and FIGS. 3A-3H.

Biosensor inserter 100 includes a push member 102 including a push element 302P that extends downwardly from the underside of push member 102 and includes a contact end that engages with a pivot member 316. The push element 302P can be a rigid member and extends downwardly (as oriented in FIG. 3A) from the underside of the push member 102. Received within the contact member 104 is a transmitter carrier 318. Transmitter carrier 318 has the wearable device 101 coupled thereto. Wearable device 101 includes a transmitter unit 110 containing at least the transmitter electronics and radio, and may include all or most of the other electronics therein. Wearable device further includes the biosensor 214B coupled thereto, which has a reading end that is received inside of the trocar 212T (see below) for insertion by the trocar 212T.

In some embodiments, the push member 102, contact member 104, pivot member 316, and/or transmitter carrier 318 may be formed from a polymer including, but not limited to, plastics such as polyethylene terephthalate (PET), high-density polyethylene (HDPE), low-density polyethylene (LDPE), polyvinyl chloride, polypropylene, polystyrene, acrylonitrile butadiene styrene (ABS), polycarbonate, nylon, acetal, polyphthalamide (PPA), polysulfone, polyethersulfone, polyetheretherketone (peek), polypropylene, and the like. Other materials may be used.

In more detail, the wearable device 101 is detachably mounted to the transmitter carrier 318 by any suitable mechanism. The transmitter carrier 318 is axially translatable relative to the contact member 104 and is configured to support the wearable device 101 during insertion of the biosensor 214B. As shown, the primary portion 101P of the wearable device 101 may include transmitter electronics, one or more power sources 232A, 232B (FIG. 2B), and a sensor assembly 214 that includes the biosensor 214B.

In some embodiments, the biosensor 214B used within the primary portion 101P may include two electrodes and the bias voltage may be applied across the pair of electrodes. In such cases, current may be measured through the biosensor 214B. In other embodiments, the biosensor 214B may include three electrodes such as a working electrode, a counter electrode, and a reference electrode. In such cases, the bias voltage may be applied between the working electrode and the reference electrode, and current may be measured through the working electrode, for example. The biosensor 214B may include an active region including one or more chemicals that undergo an analyte-enzyme reaction with the products they detect. The enzyme is immobilized on one or more electrodes to provide a reaction (e.g., redox reaction) with the analyte and generate a current at the electrodes. Example chemicals include glucose oxidase, glucose dehydrogenase, or the like for measuring glucose as an analyte. In some embodiments, a mediator such as ferricyanide or ferrocene may be employed at the active region. In general, any analyte that may be detected and/or monitored with a suitable sensor and for which suitable chemistry exists may be measured, such as glucose, cholesterol, lactate, uric acid, alcohol, or the like. An analyte is defined herein as a component, substance, chemical species, or chemical constituent that is measurable in an analytical procedure.

An example of the biosensor 214B can be any suitable implantable sensor that can be implanted in the skin of a user, such as a strand-shaped sensor that is able to be received inside of the trocar 312T of the trocar assembly 312 and that is able to sense an analyte concentration reading of an interstitial fluid under the skin.

Figure 3A:
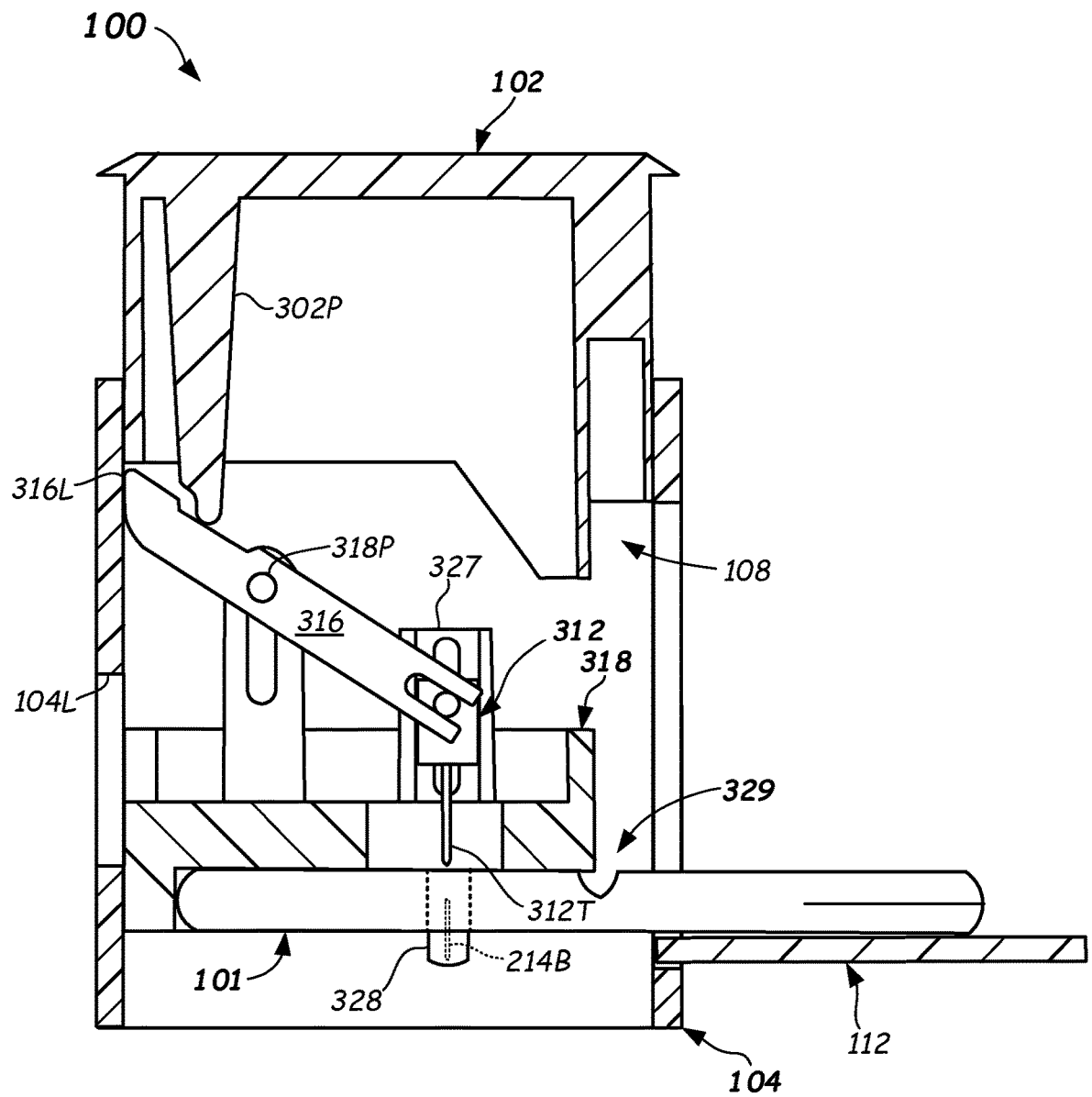
FIG. 3A is a cross-sectioned side view of a biosensor inserter illustrating a wearable device inserted in a receiver of a transmitter carrier in accordance with one or more embodiments provided herein.

The operation of the biosensor inserter 100 will now be described. In a first stage, the wearable device 101 is inserted into the opening 329 with the door 112 opened as shown in FIGS. 1A and 3A. The primary portion 101P is received in retention features on the sides of the transmitter carrier 318, such as curved features closely matching the sides of the primary portion 101P, tabs, or other features that hold the primary portion 101P sufficiently so that the secondary portion 101S can be folded, but not so tightly that the wearable device 101 cannot be removed after insertion is completed.

Figure 3B:
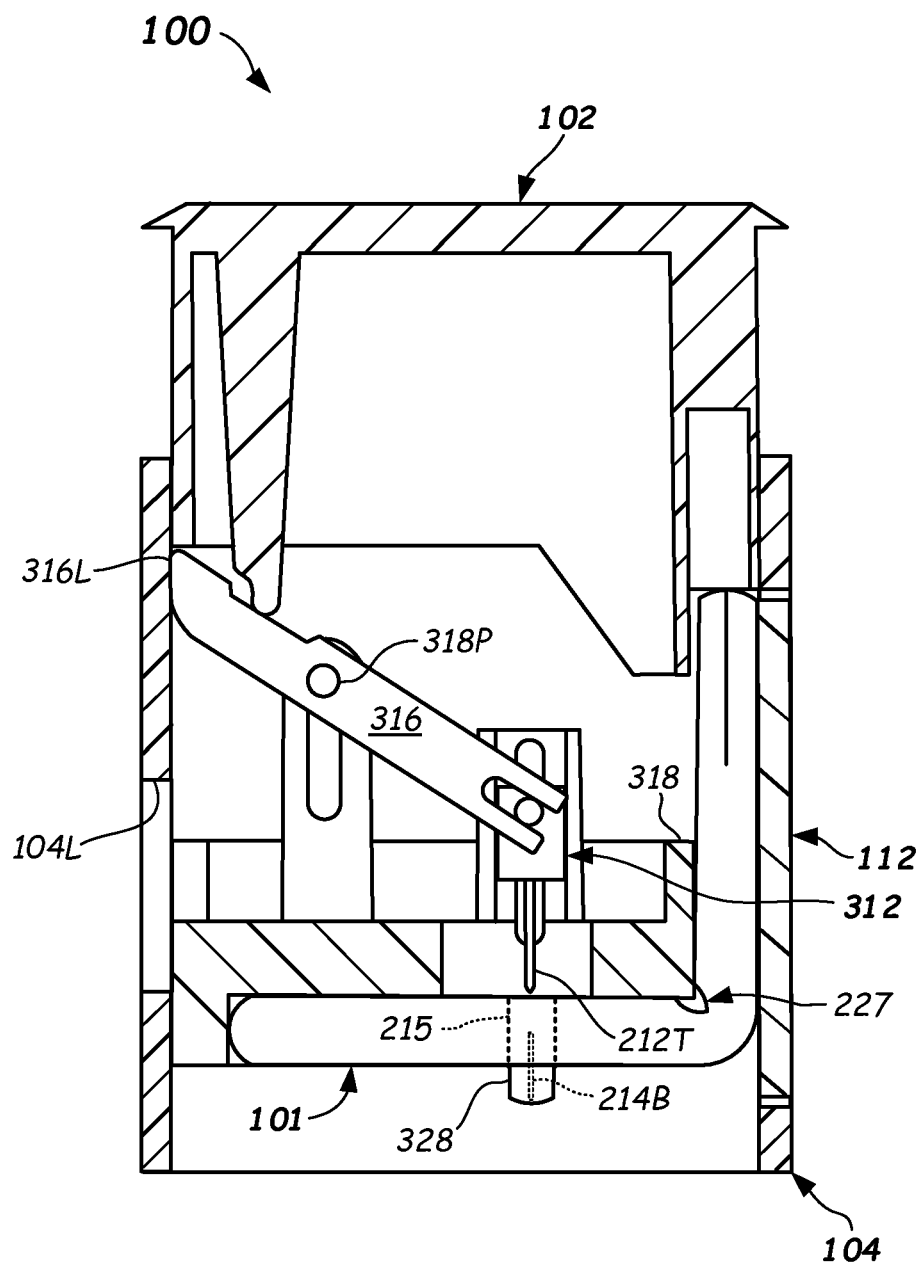
FIG. 3B is a cross-sectioned side view of a biosensor inserter illustrating the folding/bending of the wearable device about a hinge thereof and the closure of the door in accordance with one or more embodiments provided herein.

As shown in FIG. 3B, the door 112 is then closed, thus folding the wearable device 101 at the hinge 227. Door 112 may include a suitable hinge at the lower end formed by posts of the door opening that interface with holes in the lower sides of the door 112 to form a pivot location for the door 112, for example. In some embodiments, a snap fit retainer mechanism may be formed in the top of the door 112 and door opening to keep the door 112 closed. Other suitable configurations of door 112 may be used.

Figure 3C:
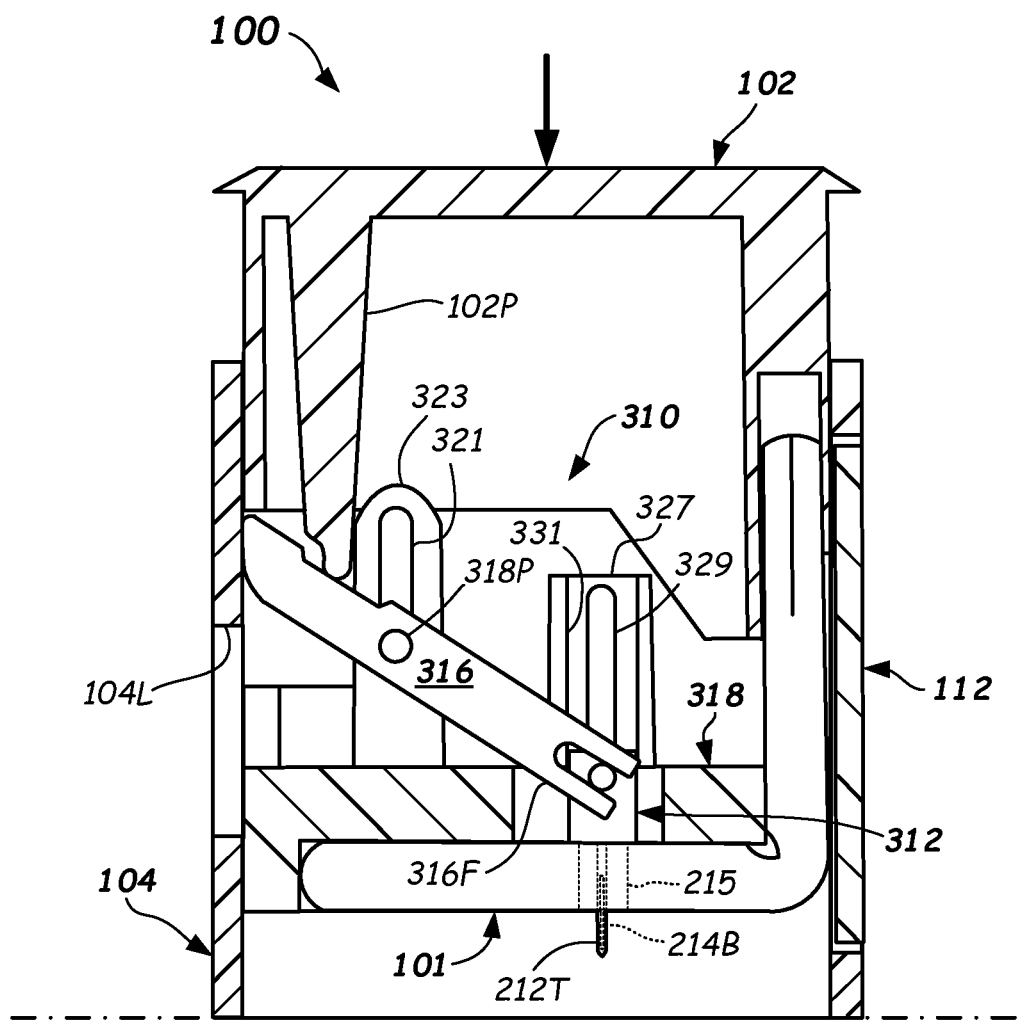
FIG. 3C is a cross-sectioned side view of a biosensor inserter illustrating the translation of the trocar assembly to receive the biosensor in an open-sided groove therein in accordance with one or more embodiments provided herein.

Next, as shown in FIG. 3C, the cover 105 (FIGS. 1A and 1B) may be removed from the biosensor inserter 100 and cap 328 may be removed from the bottom side of the wearable device 101, such as by unscrewing a threaded portion thereof, and an adhesive backing may be removed from the primary portion 101P to expose adhesive applied to that portion. The contact member 104 is placed in contact with the skin (skin shown as dot-dash line) and a force (indicated by vertically down oriented bold arrow) is applied on the push member 102 via being pushed thereon by the user (or another). This causes the pivot member 316 to translate vertically in a first portion of the stroke.

The posts of pivot member 316 extending from each lateral side thereof translate along slots 321 on side supports 323 of the transmitter carrier 318 formed on either side of the pivot member 316 (only one side shown; the other side being identical). Likewise, the trocar assembly 312 and trocar 312T are translated toward the skin during the first portion of a stroke of the biosensor inserter 100.

A pivot location of the pivot member 316 can be formed between the first end and the opposite end of pivot member 316. For example, a pivot axis may be formed by the laterally extending features, such as cylindrical posts that project from the respective lateral sides of the body of the pivot member 316. The laterally extending posts can be received in the slots 321 formed in opposite sides of the side supports 323 of the transmitter carrier 318. The pivot member 316 can include a push element interface feature, which may comprise a pocket or other interface feature formed between the pivot axis and the latch end 316L (FIG. 3E) that is configured to interface with and contact a contact end of the push element 102P as described further below. Other suitable laterally extending features may be used to form the pivot, such as a removable axle, or the like. During a first portion of an insertion stroke, pivot member 316 contacts the contact member 104 and is prevented from rotating until a second portion of the insertion stroke when the pivot member 316 passes a latch 104L. Other mechanisms that constrain rotation for the first portion of the stroke and then allow rotation for the retraction portion of the stroke may be used.

In one or more embodiments, the trocar assembly 312 includes a body 312B (FIGS. 3G and 3H) having a body geometry that rides in grooves 331 (FIG. 3C) formed on the inside of the opposed side supports 327 of the transmitter carrier 318 (only one shown, but the other is a mirror image). The body geometry of the body 312B of the trocar assembly 312 can have a rectangular body shape, that properly aligns the trocar 212T as the body 312B descends along the grooves 331 and slots 329 as the forks 316F drive the wings 312W (See FIGS. 3G and 3H). The pivot member 316 may straddle the outside of side supports 327 and engage wings 312W. During this portion of the stroke, the biosensor 214B, which extends downwardly from aperture 215 of the wearable device 101, is aligned with, and received within a lengthwise open-sided groove 332 formed in a side of the trocar 212T.

Figure 3D:
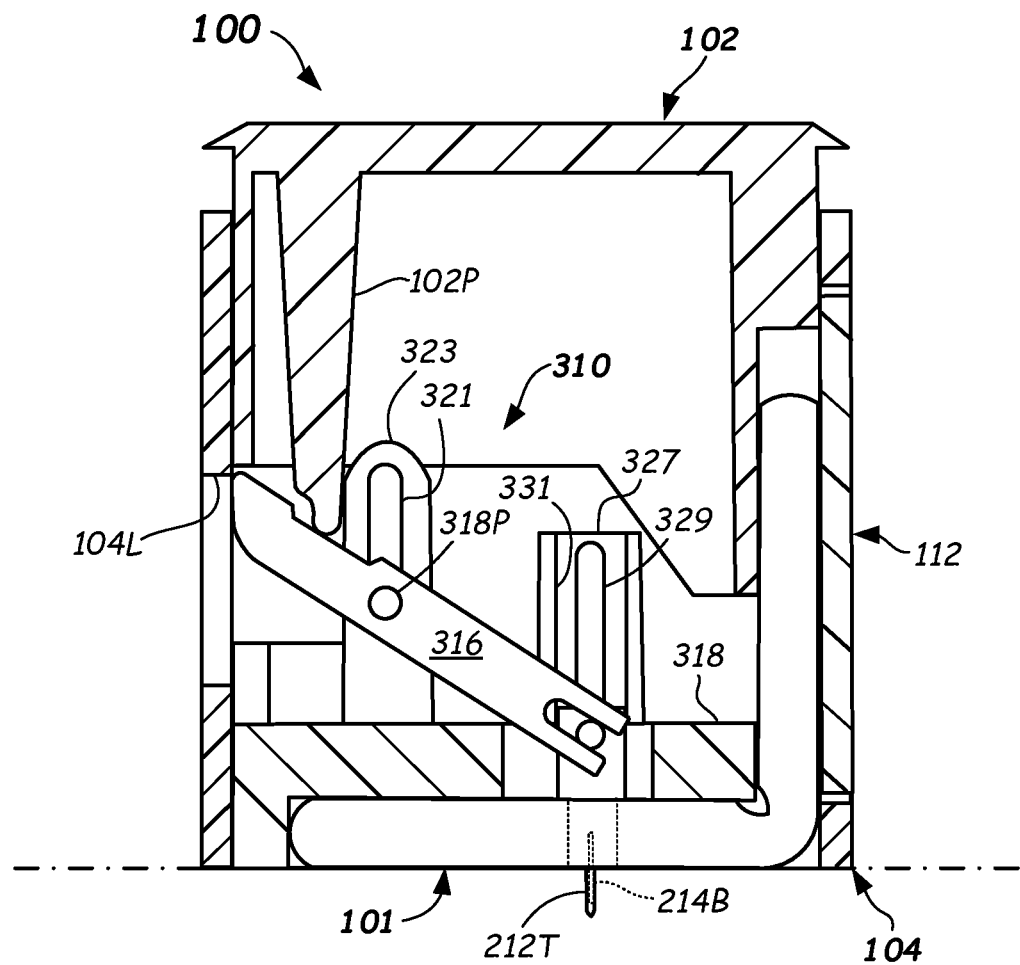
FIG. 3D is a cross-sectioned side view of a biosensor inserter illustrating the translation of the trocar assembly to insert the trocar and biosensor into the skin of the user in accordance with one or more embodiments provided herein.
Figure 3E:
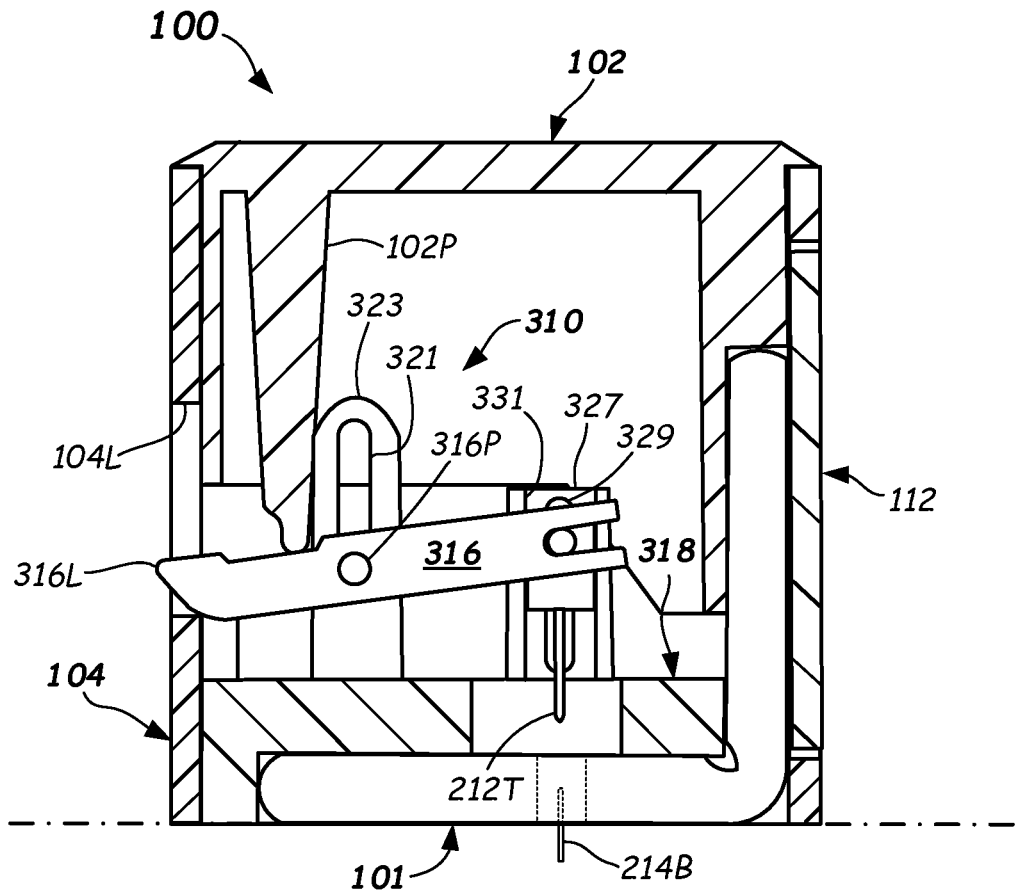
FIG. 3E is a cross-sectioned side view of a biosensor inserter illustrating the retraction of the trocar assembly to leave the biosensor inserted in the skin of the user in accordance with one or more embodiments provided herein.
Figure 3F:
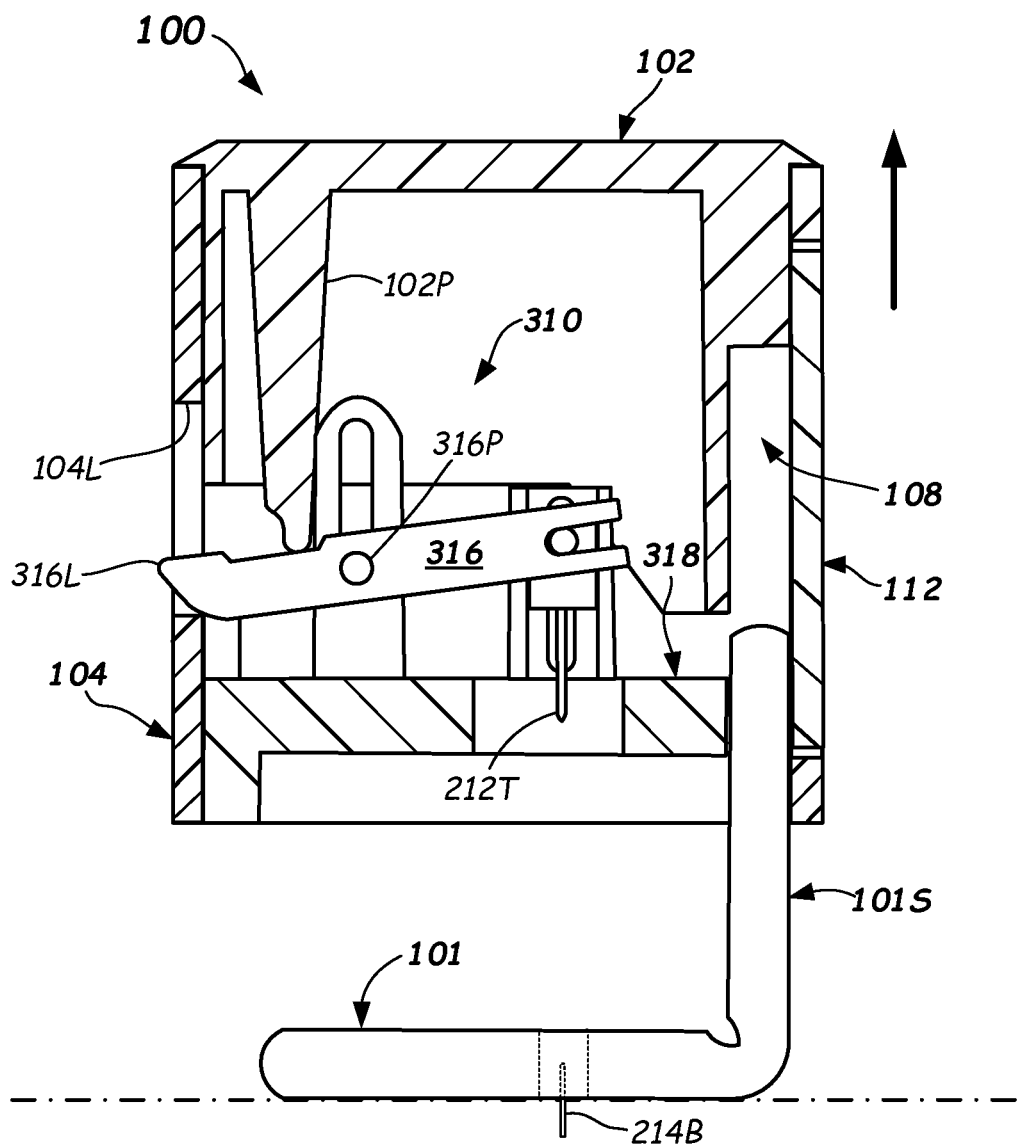
FIG. 3F is a cross-sectioned side view of a biosensor inserter illustrating separation of the biosensor inserter and the wearable device in accordance with one or more embodiments provided herein.
Figure 3G:
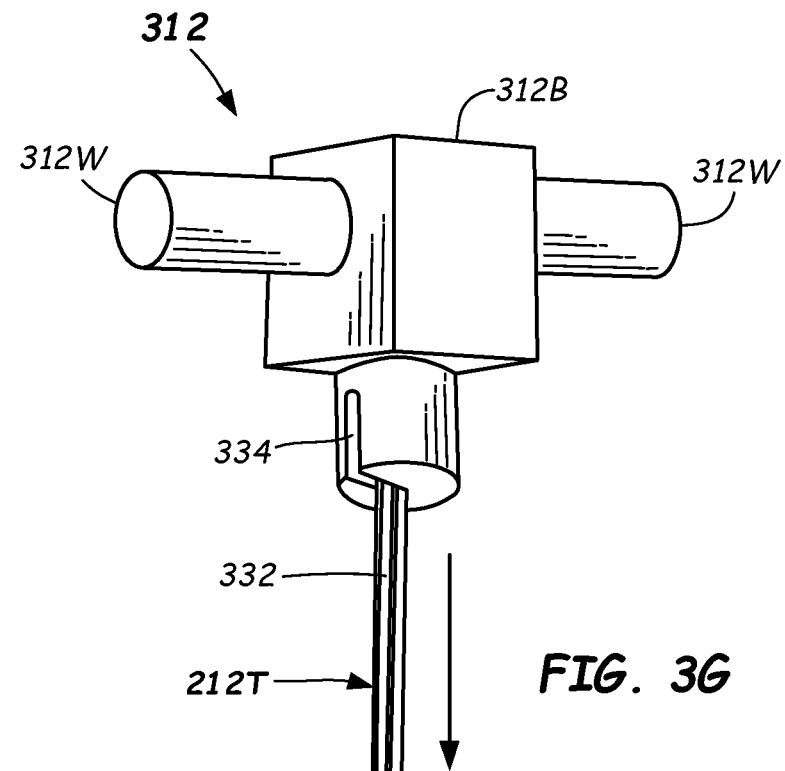
FIG. 3G is a perspective side view of a trocar assembly and sensor assembly illustrating the threading and insertion of the biosensor into the open-sided groove of the trocar in accordance with one or more embodiments provided herein.
Figure 3H:
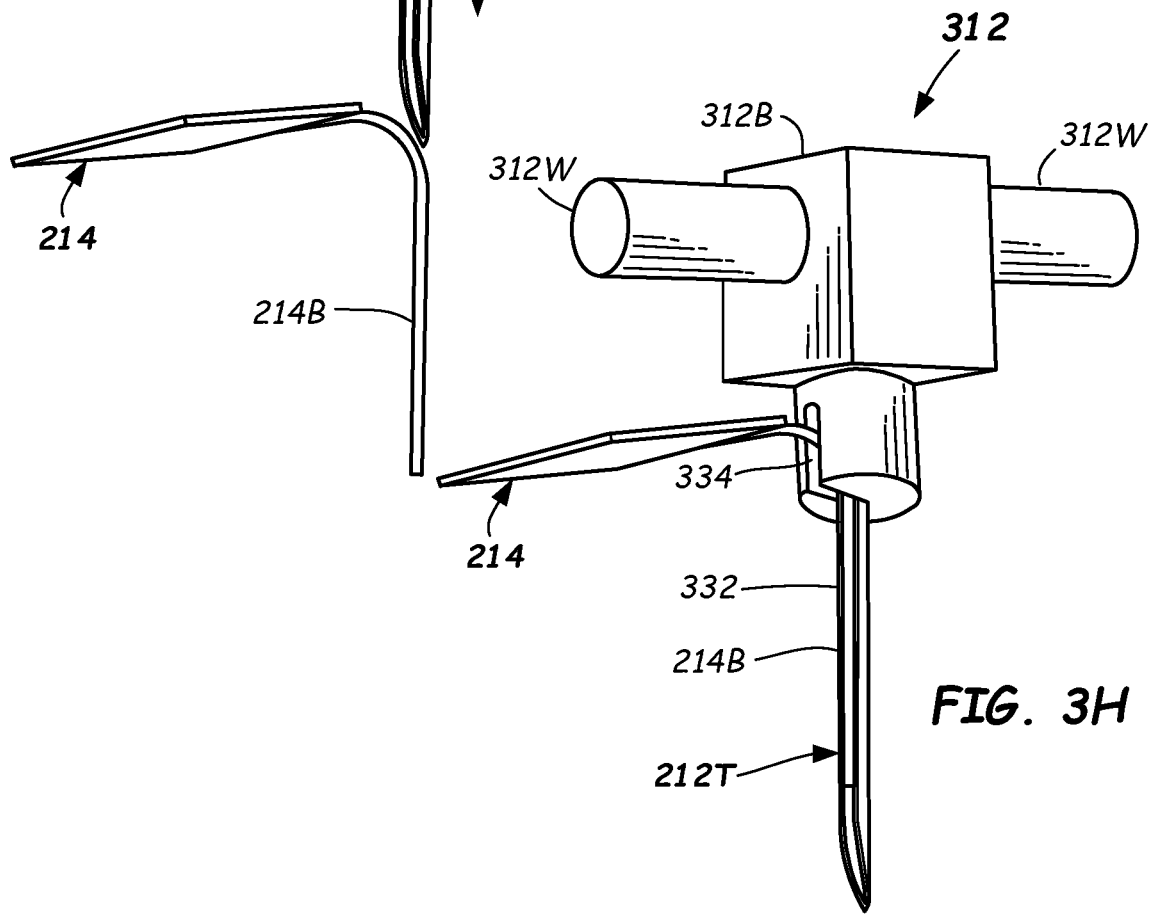
FIG. 3H is a perspective side view of a trocar assembly and sensor assembly illustrating the biosensor inserted into the open-sided groove of the trocar in accordance with one or more embodiments provided herein.

As shown in FIGS. 3G and 3H, precise alignment between the trocar 212T and the biosensor 214B as the trocar 212T descends is desirable. In some embodiments steering features may be formed in aperture 215 that may be used to steer and thus aid in ensuring that the biosensor 214B is properly aligned with and is received in the lengthwise open-sided groove 332 and body groove 334 of the trocar 212T and body 312B as shown in FIGS. 3G and 3H. FIG. 3G illustrates the sensor assembly 214 and biosensor 214B prior to insertion during the ascending of the trocar assembly 312, whereas, FIG. 3H illustrates biosensor 214B properly aligned with and received in the lengthwise open-sided groove 332 and body groove 334 of the trocar 212T and body 312B after descending.

Next, as shown in FIG. 3D, as the user continues to push on push member 102, this further translates the transmitter carrier 318 and the wearable device 101 and inserts the trocar 212T and the biosensor 214B into the skin (outer skin surface shown dotted).

Next, as shown in FIG. 3E, as the user continues to push on push member 102 the latch end 316L of the pivot member passes by latch 104L and the pivot member 316 can freely pivot about the end of slot 321 and cause the trocar assembly 312 and the trocar 212T to be retracted as shown, thus leaving the biosensor 214B implanted into the skin (outer skin surface shown dotted) while still connected to the internal electronics.

The latch 104L comprises a latch surface (lower latch surface) that once passed by via motion of a latch end 316L of the pivot member 316, will allow a pivot member 316 to rotate (FIG. 3E). Latch 104L may be formed as an opening in the sidewall of the contact member 104. The latch 104L can comprise a circumferentially disposed surface of a width wider than the latch end 316L of the pivot member 316. Up until when the latch end 316L passes by the latch 104L, the pivot member 316 is largely restrained from rotation. As shown, latch 104L is part of a vertically extending cutout that may be closed at its lower end, for example.

As shown in FIG. 3F, to separate the biosensor inserter 100 from the wearable device 101, the user can pull on the contact member 104. This pulls the secondary portion 101S from the pocket formed by relief 108 and door 112. Once the biosensor inserted 100 is completely removed, the user may remove the backing from the adhesive portion applied to the secondary portion 101S and fold the secondary portion 101S onto the skin and apply slight pressure to adhere the adhesive to the skin (See FIG. 9).

Once removed, all of the biosensor inserter 100 can be discarded as medical waste. Because the footprint has been dramatically reduced, the volume, and thus cost, of the material is also dramatically reduced.

As should be understood, contact member 104 may be configured to be concentric with push member 102 and may be telescopic therewith. In some embodiments, push member 102 may include a first alignment feature such as a vertically extending groove or recess, and contact member 104 may include a second alignment feature, such as a vertically extending rib, that interfaces with the first alignment feature. Such alignment features may hold push member 102 and contact member 104 in rotational alignment to prevent rotation of the contact member 104 within the push member 102, such as during the insertion and retraction portions of the stroke. Push member 102 and contact member 104 may be cylindrical, oval, oblong, elliptical, or any other suitable shape in transverse cross-section. In some embodiments, push member 102 and contact member 104 may not be concentric.

Referring now to FIG. 4 through FIG. 11, an embodiment of a method 1100 of using a biosensor inserter (e.g., biosensor inserter 100) to insert a biosensor (e.g., biosensor 214B) is described. The method 1100 comprises, in block 1102, providing the biosensor inserter comprising: a push member (e.g., push member 102), a contact member (e.g., contact member 104) translatable relative to the push member, a trocar assembly (e.g., trocar assembly 312) including a trocar (e.g., trocar 212T), and a relief (e.g., relief 108) formed in the push member or contact member, the relief configured to allow a secondary portion (e.g., secondary portion 101S) of a wearable device (e.g., wearable device 101) to be folded into the relief, and a mechanism (e.g., mechanism 310) configured to translate the wearable device 101 and insert the trocar.

Figure 6:
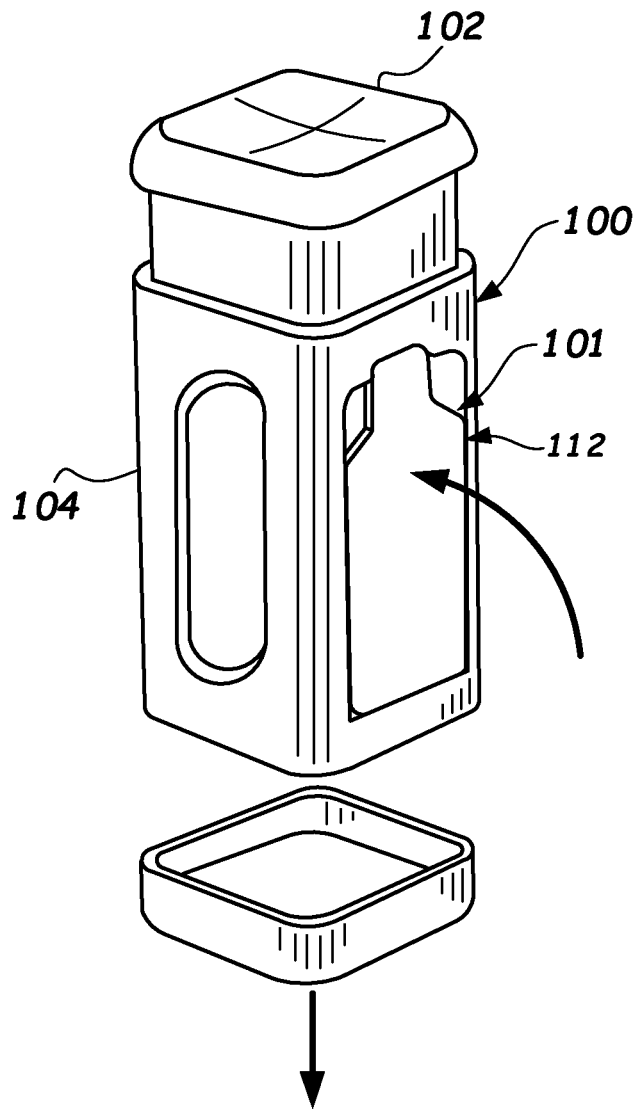
FIG. 6 is a perspective view of a biosensor inserter illustrating a cap being removed and the door shut thus folding a secondary portion including the transmitter unit of the wearable device into a relief in accordance with one or more embodiments provided herein.

The method 1100 further includes, in block 1104, folding the secondary portion (e.g., secondary portion 101S) of the wearable device into the relief as shown in FIG. 6 via closing door 112, and in block 1106, contacting the contact member (e.g., contact member 104) to a person's skin 750, and, in block 1108, pushing on the push member (e.g., push member 102) during a first portion of a stroke to cause translation of the wearable device and implantation of the trocar and biosensor.

Figure 7:
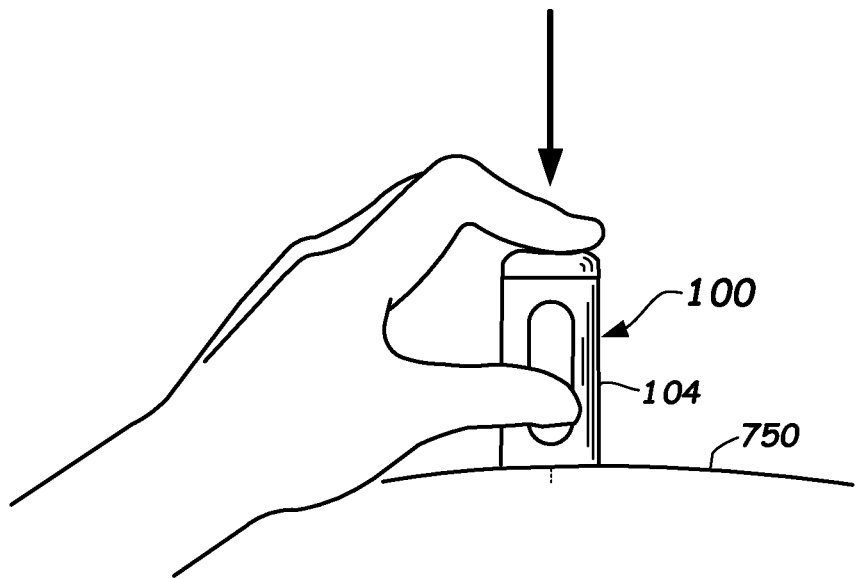
FIG. 7 is a side view of a biosensor inserter illustrating a person pushing on a push member to insert a biosensor of the wearable device into the skin in accordance with one or more embodiments provided herein.

The method 1100 comprises, in block 1110, continuing to push the push member causing the mechanism to retract the trocar assembly while leaving the biosensor implanted during a second portion of the stroke as is shown in FIG. 7.

Figure 4:
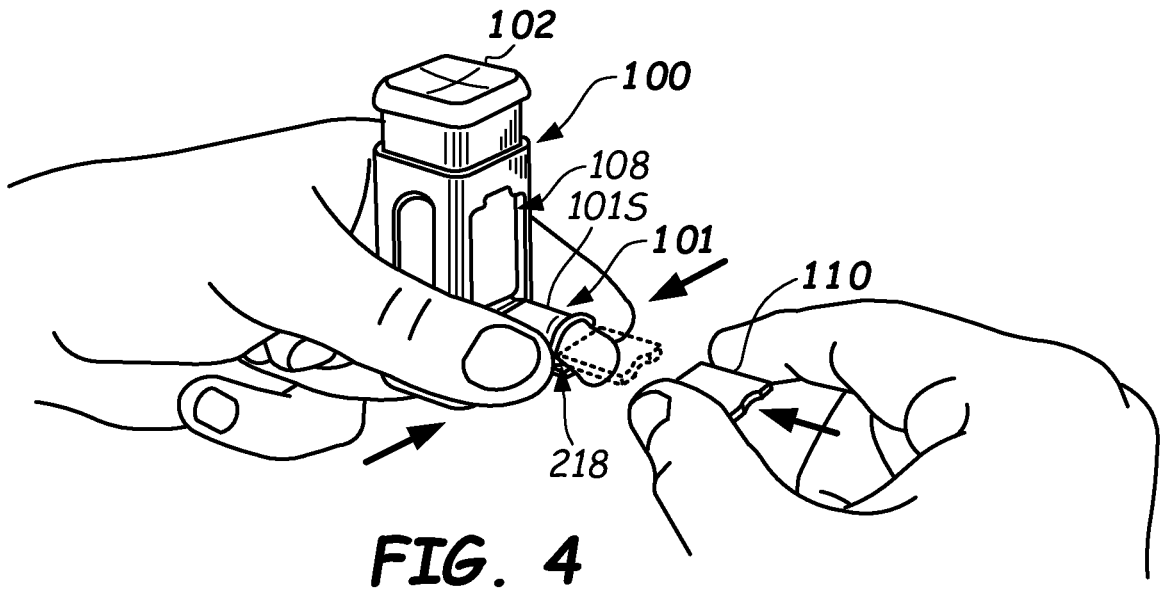
FIG. 4 is a perspective view of a biosensor inserter illustrating insertion of a transmitter unit into a pocket of the wearable device in accordance with one or more embodiments provided herein.
Figure 5:
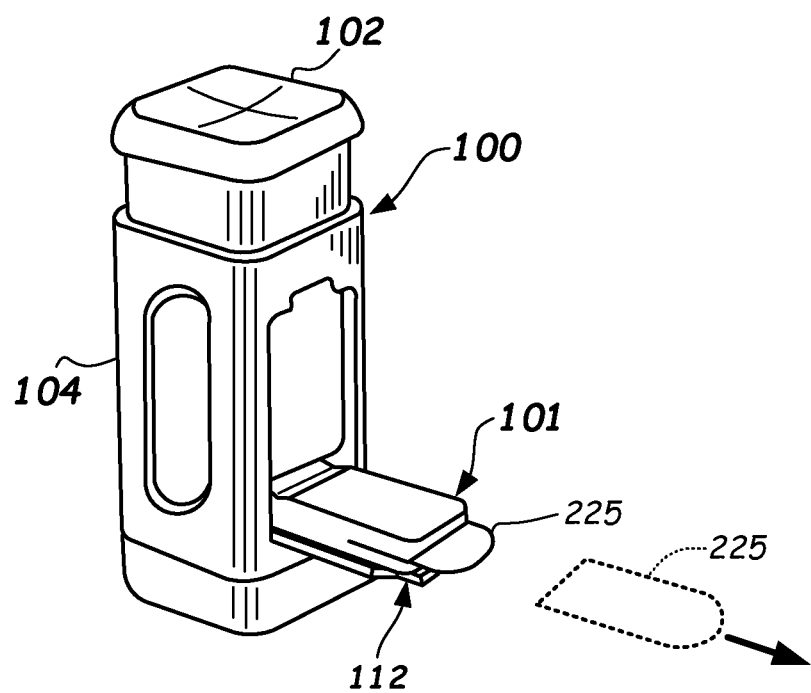
FIG. 5 is a perspective view of a biosensor inserter illustrating removal of a backing member to expose adhesive and thus enable sealing of the opening to the pocket in accordance with one or more embodiments provided herein.
Figure 8:
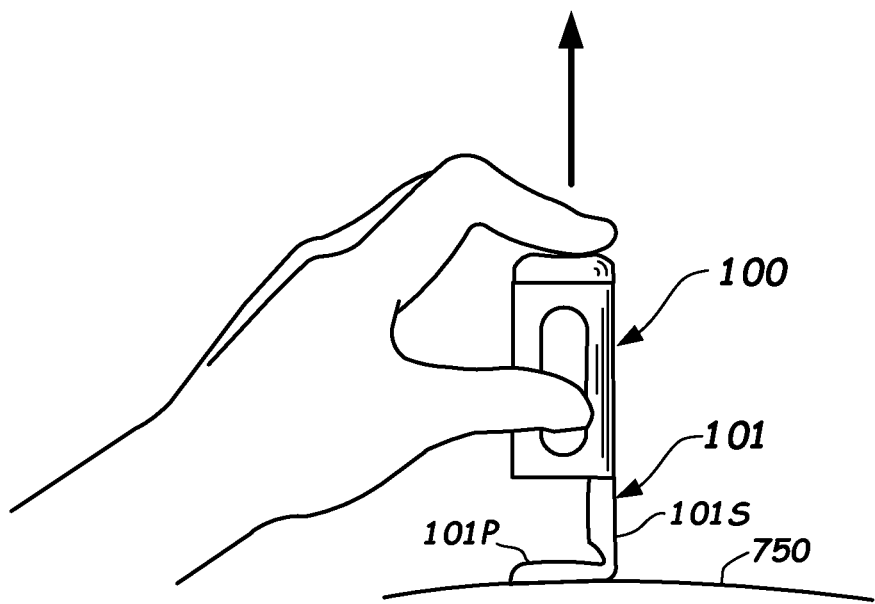
FIG. 8 is a side view of a biosensor inserter illustrating removal of the biosensor inserter and exposing the wearable device in a folded condition in accordance with one or more embodiments provided herein.
Figure 9:
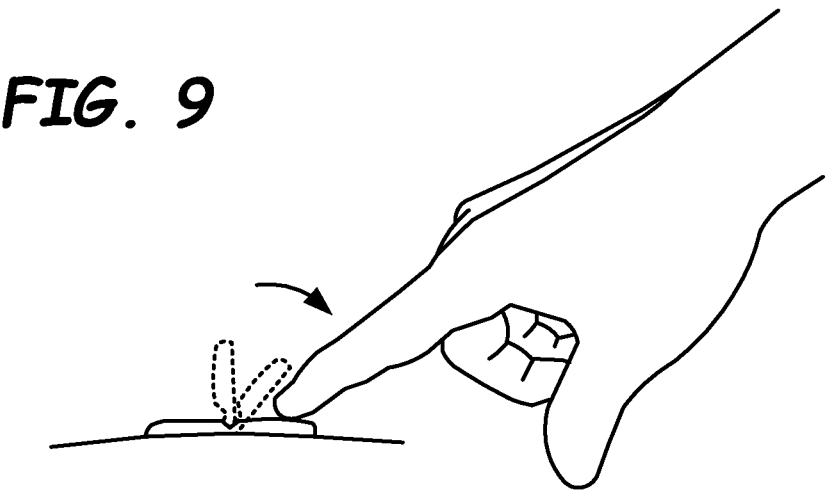
FIG. 9 is a side view of a person unfolding and then adhering the secondary portion of the wearable device to the skin in accordance with one or more embodiments provided herein.
Figure 10:
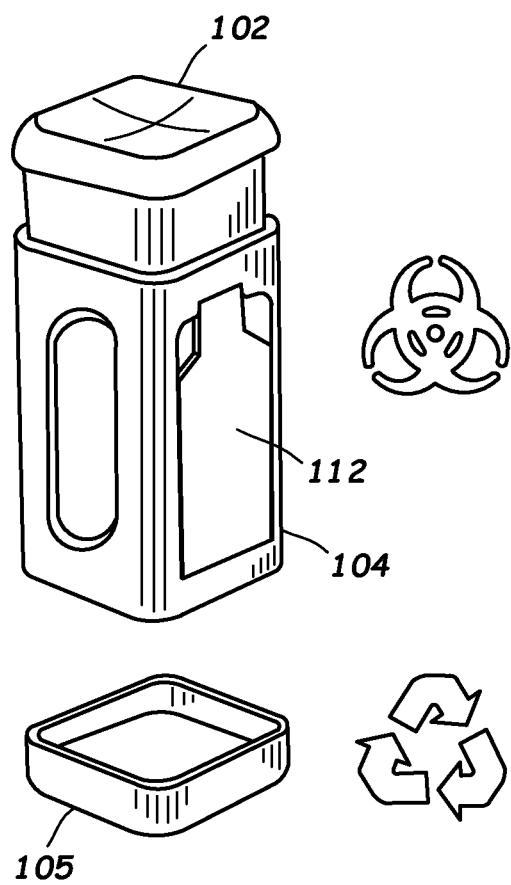
FIG. 10 is a perspective view illustrating the medical waste and the recyclable components of the biosensor inserter in accordance with one or more embodiments provided herein.
Figure 11:
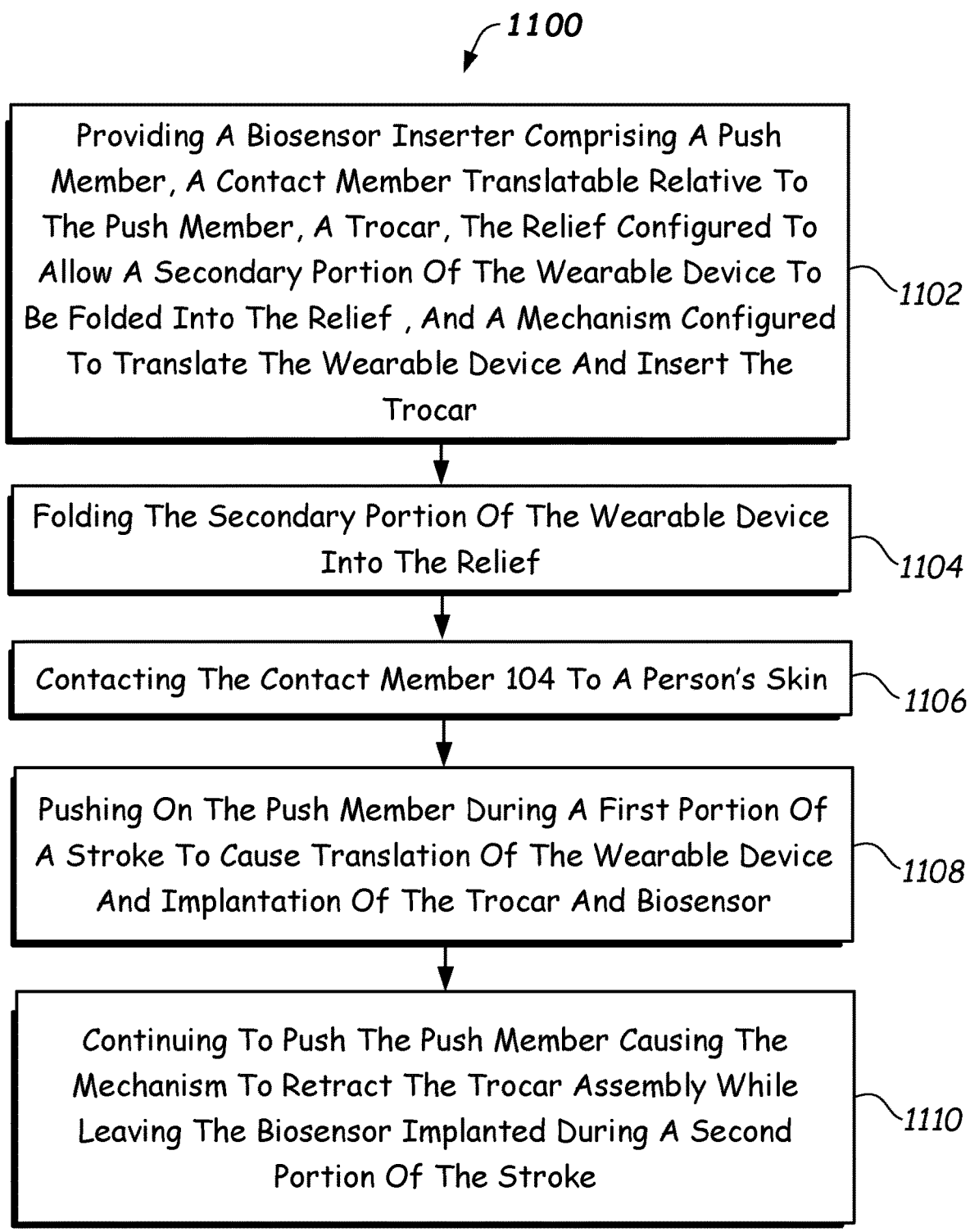
FIG. 11 illustrates a flowchart of a method of using a biosensor inserter to insert a biosensor in accordance with embodiments provided herein.

Prior to folding the secondary portion 101S of the wearable device 101 into the relief 108, the method 1100 can involve inserting a transmitter unit 110 into a pocket 216 (FIG. 2F) formed in the secondary portion 101S through an opening 218, such as through slit opening shown in FIG. 4. Sides of the secondary portion can be squeezed with a thumb and finger to allow access to the opening 218. Pocket 216 may be of sufficient size to receive the entire volume of the transmitter unit 110 therein. The method 1100 may further include coupling the transmitter unit 110 to an electrical connector 234 provided in the pocket 216. The electrical connector 234 may be a pogo-type electrical connector or other suitable connector. According to the method 1100, the opening 218 of the secondary portion 101S may be sealed. In some embodiments, the sealing comprises removing a backing member 225 to expose adhesive 220 applied on edges 222 of the opening 218 (See FIGS. 5 and FIGS. 2D-2F). Slight pressure to the edges 222 can seal the opening 218 and hermetically seal the transmitter unit 110 into the pocket 216. After separation of the wearable device 101 from the biosensor inserter 100 as shown in FIG. 8, the secondary portion 101S can be unfolded and adhered to the skin as shown in FIG. 9. After separation of the biosensor inserter 100 from the wearable device 101, the biosensor inserter 100 can be disposed of as medical waste, whereas the cover 105.

The foregoing description discloses only example embodiments. Modifications of the above-disclosed apparatus and methods, which fall within the scope of this disclosure, will be readily apparent to those of ordinary skill in the art.

What is claimed is:

1. A continuous analyte monitor wearable device, comprising:
    a primary portion comprising at least a sensor assembly comprising a biosensor;
    a secondary portion comprising a pocket configured to receive a reusable transmitter unit through a sealable opening to the pocket, the sealable opening comprising a first flap, a second flap, and an adhesive;
    wherein the first flap and the second flap are configured to be flexed apart such that the reusable transmitter unit is receivable between the first flap and the second flap;
    a backing member provided over the adhesive wherein removal of the backing member exposes the adhesive to seal the first flap and the second flap to one another such that the sealable opening is sealed and encapsulates the reusable transmitter unit; and
    a hinge formed by a first end of the primary portion and a second end of the secondary portion configured to allow the secondary portion to bend locally at the hinge and fold such that the secondary portion is perpendicular to the primary portion, wherein the continuous analyte monitor wearable device is configured to fit within a biosensor inserter by inserting the primary portion into the biosensor inserter, the biosensor inserter folding the secondary portion about the hinge such that the secondary portion is perpendicular to the primary portion within a relief of the biosensor inserter.

2. The continuous analyte monitor wearable device of claim 1, wherein the hinge comprises a foldable portion of a circuit board.

3. The continuous analyte monitor wearable device of claim 1, wherein the hinge comprises a trough formed in a body and extending between sides of the body of the continuous analyte monitor wearable device.

4. The continuous analyte monitor wearable device of claim 1, wherein the primary portion further comprises one or more power sources.

5. The continuous analyte monitor wearable device of claim 1, wherein the pocket in the secondary portion further comprises an electrical connector.

6. The continuous analyte monitor wearable device of claim 5, wherein the electrical connector comprises a pogo pin connector.

7. The continuous analyte monitor wearable device of claim 1, wherein the biosensor is received through an opening in a circuit board.

8. The continuous analyte monitor wearable device of claim 1, wherein the pocket contains the reusable transmitter unit.

9. The continuous analyte monitor wearable device of claim 1, wherein the primary portion further comprises a circuit board comprising an opening, wherein the opening at least partially receives the biosensor.

10. The continuous analyte monitor wearable device of claim 1, wherein the backing member comprises an exposed end to facilitate the removal of the backing member.

11. A system for inserting a biosensor, comprising:
    a continuous analyte monitor wearable device comprising:
        a primary portion comprising at least a sensor assembly comprising the biosensor;
        a secondary portion comprising a pocket configured to receive a reusable transmitter unit through a sealable opening to the pocket, the sealable opening comprising a first flap, a second flap, and an adhesive;
        wherein the first flap and the second flap are configured to be flexed apart such that the reusable transmitter unit is receivable between the first flap and the second flap;
        a backing member provided over the adhesive wherein removal of the backing member exposes the adhesive to seal the first flap and the second flap to one another such that the sealable opening is sealed and encapsulates the reusable transmitter unit; and
        a hinge formed by a first end of the primary portion and a second end of the secondary portion configured to allow the secondary portion to bend locally at the hinge and fold such that the secondary portion is perpendicular to the primary portion; and
    a biosensor inserter comprising:
        a push member;
        a contact member translatable relative to the push member; and
        a relief formed in the push member or the contact member, the relief configured to allow the secondary portion of the continuous analyte monitor wearable device to be folded into the relief such that the secondary portion is perpendicular to the primary portion.

12. The system of claim 11, wherein the push member or the contact member comprises a door that provides access to the relief.

13. The system of claim 12, wherein the continuous analyte monitor wearable device is insertable into the biosensor inserter when the door is in an open configuration.

* * * * *